(12) United States Patent
Guendel

(10) Patent No.: US 6,501,820 B2
(45) Date of Patent: Dec. 31, 2002

(54) X-RAY CT APPARATUS AND METHOD FOR OPERATING SAME FOR REDUCING THE RADIATION DOSE TO AN EXAMINER HAVING A BODY PART EXPOSED TO THE X-RAY BEAM

(75) Inventor: Lutz Guendel, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 83 days.

(21) Appl. No.: 09/760,051

(22) Filed: Jan. 13, 2001

(65) Prior Publication Data

US 2001/0019599 A1 Sep. 6, 2001

(30) Foreign Application Priority Data

Jan. 14, 2000 (DE) .......................................... 100 01 357

(51) Int. Cl.[7] .................................................. A61B 6/00
(52) U.S. Cl. .......................................... 378/15; 378/16
(58) Field of Search ................................ 378/15, 16, 8, 378/4

(56) References Cited

U.S. PATENT DOCUMENTS

| | | | |
|---|---|---|---|
| 5,841,830 A | 11/1998 | Barni et al. .................... | 378/15 |
| 5,867,555 A | 2/1999 | Popescu et al. ................ | 378/16 |
| 5,873,826 A | 2/1999 | Gono et al. .................. | 600/425 |
| 6,292,527 B1 * | 9/2001 | Guendel ....................... | 378/15 |
| 6,320,929 B1 * | 10/2001 | Von Der Harr ................ | 378/4 |
| 6,343,109 B2 * | 1/2002 | Doubrava et al. ............. | 378/4 |

\* cited by examiner

Primary Examiner—Robert H. Kim
Assistant Examiner—Irakli Kiknadze
(74) Attorney, Agent, or Firm—Schiff Hardin & Waite (57) ABSTRACT

In a method and CT device for scanning an examination subject, a radiation beam emanates from a focus of a radiation source which can be displaced around a system axis and strikes a detector system. If, during scanning, a body part of an examiner moves into an examination space covered by the radiation beam, this is automatically detected and the effective radiation is automatically reduced for a volumetric region which includes the body part of the examiner, with respect to a comparable second volumetric region, in which no body part of the examiner is located. The effect of this is to diminish the radiation dose to the examiner. Control for this purpose is performed, for example, by varying the tube current, by adjusting a beam diaphragm, or by an absorber inserted into the beam path. A parameter associated with the body part of the examiner also is detected and the size of the first volumetric region is automatically adjusted dependent on this parameter.

16 Claims, 6 Drawing Sheets

X-RAY CT APPARATUS AND METHOD FOR OPERATING SAME FOR REDUCING THE RADIATION DOSE TO AN EXAMINER HAVING A BODY PART EXPOSED TO THE X-RAY BEAM

BACKGROUND OF THE INVENTION

1. Field of the Invention

The present invention relates to a method for scanning an examination subject using a CT device with a radiation source with a focus which can be displaced around about a system axis with a radiation beam emanating from the focus and striking a detector system which produces scanning data, and wherein the effective radiation is a first volumetric region, in which a body part of an examiner is located during the scanning, is reduced with respect to the effective radiation in a comparable second volumetric region of the same size and at the same distance from the system axis in which no body part of the examiner is located.

2. Description of the Prior Art

CT devices and known which have a radiation source, for example an X-ray tube, which directs a collimated, pyramidal radiation beam through the examination subject, for example a patient, onto a detector system assembled from a number of detector elements. The radiation source and, depending on the design of the CT device, the detector system as well, are fitted on a gantry which rotates around the examination subject. A support device for the examination subject can be displaced or moved along the system axis relative to the gantry. The starting position from which the radiation beam penetrates the examination subject, and the angle at which the radiation beam penetrates the examination subject, are continuously varied as a consequence of the rotation of the gantry. Each detector element of the detector system, when struck by the radiation, produces a signal which constitutes a measure of the total transparency of the examination subject for the radiation emanating from the radiation source on its path to the detector system. The set of output signals of the detector elements of the detector system, which set is obtained for a specific position of the radiation source, is known as a projection. A scan comprises a set of projections which have been obtained at different positions of the gantry and/or different positions of the support device. The CT device picks up a multiplicity of projections during a scan, in order to be able to build up a two-dimensional tomographic image of a section of the examination subject. A number of sections can be picked up simultaneously with using a detector system formed as an array of a number of rows and columns of detector elements.

Relatively large volumes of the examination subject are usually picked up by means of sequential scanning or spiral scanning. In the case of sequential scanning, the data are picked up during the rotary movement of the gantry, while the examination subject is located in a fixed position, and thus planar sections are scanned. The examination subject is moved between the scanning of successive sections into a new position in which the next section can be scanned. This process continues until all sections designated before the examination are scanned. In the case of spiral scanning, the gantry rotates continuously with the radiation source around the examination subject, while the support table and the gantry are continuously displaced relative to one another along a system axis. Relative to the examination subject, the radiation source therefore describes a spiral path until the volume designated before the examination has been scanned. Images of individual sections are then calculated from the spiral data.

Furthermore, CT devices are known in the case of which the X-ray power can be modulated during the rotation of the radiation source around the examination subject with a non-circular cross section in order to scan the examination subject. If, for example, a patient lying on his or her back is being scanned, as a rule the path of the X-ray radiation through the body of the patient is longer in the horizontal direction than in the vertical direction. If a modulation of the X-ray power is not possible, the power must be set such that the signal quality supplied by the detector system is still sufficient to calculate correct images even for the projections with the longest path of the radiation through the body. The X-ray power therefore is unnecessarily high for all other projections. In order not to stress the object under examination with an excessive radiation dose, an attempt is made to set the X-ray power in accordance with the attenuation profile as a function of the angular position of the radiation source. Such a method is described, for example, in German OS 19 806 063.

CT devices are used principally in the field of medicine. In addition to examinations for purely diagnostic purposes, interventions (for example biopsies, centeses) are increasingly being carried out with the aid of CT monitoring. During the intervention, the position of medical instruments required to carry out the intervention, for example a needle, can thus be monitored continuously. When a radiation source is switched on and manual guidance of such a medical instrument is employed by an examiner, body parts of the examiner, for example a hand, which are located in the region penetrated by the radiation beam between the focus and detector system can be struck by unattenuated radiation.

U.S. Pat. No. 5,873,826 discloses an X-ray CT device wherein the radiant power of the X-ray source can be temporarily reduced during scanning in order to reduce the radiation dose to an examiner. The volumetric region for which this reduction is effective is designated before scanning, and is identified during scanning by marking with a light source.

U.S. Pat. No. 5,841,830 discloses a CT device wherein diagnostic image information is obtained with x-rays at a first intensity, and image information relating to the movement of an invasive surgical instrument is obtained with x-rays at a second intensity, reduced by comparison with the first intensity. The diagnostic image information and the image information relating to the movement of the surgical instrument are superimposed to form a resulting image.

SUMMARY OF THE INVENTION

An object of the present invention is to provide a method for operating a CT device such that the radiation dose to an examiner is reduced and, at the same time, a good quality of the calculated images is achieved. It is also an object of the invention to provide a CT device for carrying out the method.

The above object is achieved in accordance with the principles of the present invention an x-ray CT apparatus of the type described above, and a method for operating such a CT apparatus, wherein movement of a body part of an examiner into an examination region covered by the x-ray beam is automatically detected, and the effective radiation is automatically reduced for a first volumetric region which includes the body part of the examiner, with respect to a comparable second volumetric region in which no body part of the examiner is located. The radiation dose to the examiner is thereby reduced. The size of the first volumetric region is automatically adjusted dependent on a detected size and/or position and/or movement direction of the body part. The adjustment of the effective radiation in the volumetric region in which the body part is located can be achieved by varying the tube current of the x-ray tube, by adjusting a beam diaphragm through which the radiation beam passes, or by inserting a radiation absorber into the beam path.

An important advantage of the inventive method and apparatus is that the radiation dose to the examiner is reduced without the examiner needing to define, before starting the scanning, a volumetric region inside the examination space into which the examiner will bring one or more body parts during the examination. The invention thus advantageously simplifies the operation of the CT device, and incorrect inputs are prevented. The invention provides a further advantage by allowing the size of the volumetric region for which the effective radiation is reduced to be limited to a minimum. This is because, for the personal safety of the examiner, the examiner need not establish, before the examination, a relatively large region which he or she must (as far as possible) not exit. The method according to the invention also eliminates the continuous and troublesome monitoring during the examination as to whether this region has actually been exited.

Without limiting the scope of the invention, it is assumed in the further description that the body part of the examiner which is located in the examination space of the CT device is his or her hand.

Various possibilities exist in order automatically to limit the region in which the examiner's hand is located and for which the radiation intensity is to be reduced. In one version of the invention the position of the hand along the system axis is detected and taken into account when generating the aforementioned parameters. In another version of the invention the angular range of the segment in which the examiner's hand is located is automatically detected and taken into account when generating the parameters. In this case, the spacing of the hand from the radiation source, and the positions of the focus, the examination subject and the hand relative to one another also can be taken into account. Thus, for example, it is possible with undiminished radiation intensity to obtain X-ray images in the angular range in which the examination subject is situated between the focus and the hand. The radiation intensity is reduced only for the angular region in which the hand is located between the focus and the examination subject. This has the advantage that most of the projections can be obtained without loss of quality during revolution of the radiation source through 360° around the examination subject. This therefore involves only a relatively light radiation stress burden for the examiner because in the case of projections where the examination subject is situated between the focus and the examiner, the radiation intensity is already attenuated by the examination subject and the spacing between the focus and the examiner is also relatively large for these projections. Since the radiation dose decreases with the square of the distance from the focus, the final outcome for these projections is only a slight radiation stress for the examiner, while still achieving good quality of the projections. In this version, as well, the region for which the radiation intensity is to be reduced can be established simply and quickly by determining a few parameters. Of course, a combination of the above versions also can be used for the automatic generation of parameters. Thus, the z-position, the angular range and the spacing of the hand from the system axis can be detected jointly in order to generate corresponding parameters.

For the purpose of automatically detecting the position of the examiner's hand in the examination space of the CT device, the CT device has a suitable detection and evaluation system. Such navigation systems for determining the position and movement of objects are sufficiently known. Their mode of operation can be based on different methods such as optical, magnetic or electromagnetic methods. Of course, it is also possible for this purpose to evaluate the data generated by the CT device itself during scanning.

The automatic dimensioning of the region penetrated by the radiation beam, and in which the examiner's hand is located, using a detection and evaluation system, has the advantage that such a system can significantly more accurately determine this region and adapt it dynamically during scanning than would be possible if this were done manually by the examiner. The system reacts immediately to movements of the hand in the examination space, and a corresponding adaptation of the region with reduced radiation is performed. Consequently, the extent of this region always can be kept relatively small. A control unit is connected between the computer of the CT device and the radiator assembly (radiation source, radiation diaphragm, etc.) for processing the data generated by the detection and evaluation system and for controlling the radiation intensity, for example, on this basis.

The radiation dose to which the examiner is subjected can be reduced in various ways. In a first embodiment, for this purpose the radiant power of the radiation source is temporarily reduced during rotation around the examination subject. The radiation source is usually an X-ray tube, for which the radiant power can be varied by influencing the tube current. The overall dynamic range of the X-ray tube from zero to a maximum radiation intensity is available in this case for control. Also possible are signal characteristics which change discontinuously or continuously, for example sinusoidal signal characteristics, as well as periodic signal characteristics. Thus, any desired radiation intensity between zero and a maximum value can be set for each z-position and each angular position in the examination space.

The invention provides a further possibility for reducing the radiation intensity by temporarily constricting size of the radiation beam in a plane perpendicular to the radiation propagation direction. This constriction size of the radiation beam reduces the angular range, and thus the period of time, in which the examiner is exposed to the radiation. This also has the effect of diminishing the applied radiation dose. The constriction of the radiation beam can be produced by adjusting a radiation diaphragm at the tube. The constriction can remain the same for a specific z-region, but also can be dynamically adjustable during a revolution of the radiation source around the examination subject. In this case, the radiation beam can be blocked out entirely or partially in a specific angular range and/or z-region. It also is possible to adopt asymmetric diaphragm settings.

In another version of the invention, the radiation intensity in the relevant region is reduced by inserting an absorber between the focus and the hand. It is advantageous in this version for the absorber to remain essentially fixed after being positioned. Once the absorber is correctly positioned, there is a need, as a rule, for only small corrections during scanning. This has a positive effect on the quality of the images produced, since it is possible to avoid the acceleration of relatively large masses during scanning as is necessary, for example, for the dynamic adjustment of diaphragm plates for temporarily constricting the radiation beam. The magnitude of the reduction in the radiation intensity by the absorber can be established by the absorber material and the thickness of the absorber. This magnitude also can have a range from a slight reduction to a complete blocking of the radiation. In addition to an absorber which is fixed after being positioned, it is possible to have an absorber which rotates with the radiation source.

A combination of the above versions for reducing the radiation dose applied to the examiner also can be used. Thus, it is possible during scanning both to constrict the radiation beam, and to lower the radiant power of the X-ray tube, for a specific region.

Reducing the radiation intensity required for carrying out scanning correctly leads as a rule to a loss in quality of the images produced. It is expedient for this loss in quality to be kept as low as possible. The invention offers the possibility of achieving this by obtaining data that are missing from projections with reduced radiation by interpolating data from projections with normal radiation. This can be done effectively, in particular, when the relevant region of the object under examination is small. In another embodiment missing data of projections with reduced radiation at least partially replaced by data from projections which were acquired without the reduction. For this technique, however, it is assumed that the examination subject does not move with respect to the support device. This technique is based on the fact that instruments used for the intervention are very easily visible, with a high contrast in the calculated images, and that movement of such instruments therefore can be followed easily, even in the case of diminished radiation intensity, whereas the examination subject does not change position and the data relating to the examination subject can be used from projection-to-projection.

In a further version of the method according to the invention, missing data of projections with reduced radiation can be calculated from data of complementary projections. In this case, a projection complementary to a given projection means a projection in which the radiation source is offset by 180° in the circumferential direction. In the case of radiation intensity being reduced only for a specific angular range, the data calculated therefrom are of high quality as a rule and are therefore well suited for producing images.

DESCRIPTION OF THE PREFERRED EMBODIMENTS

Figure 1:
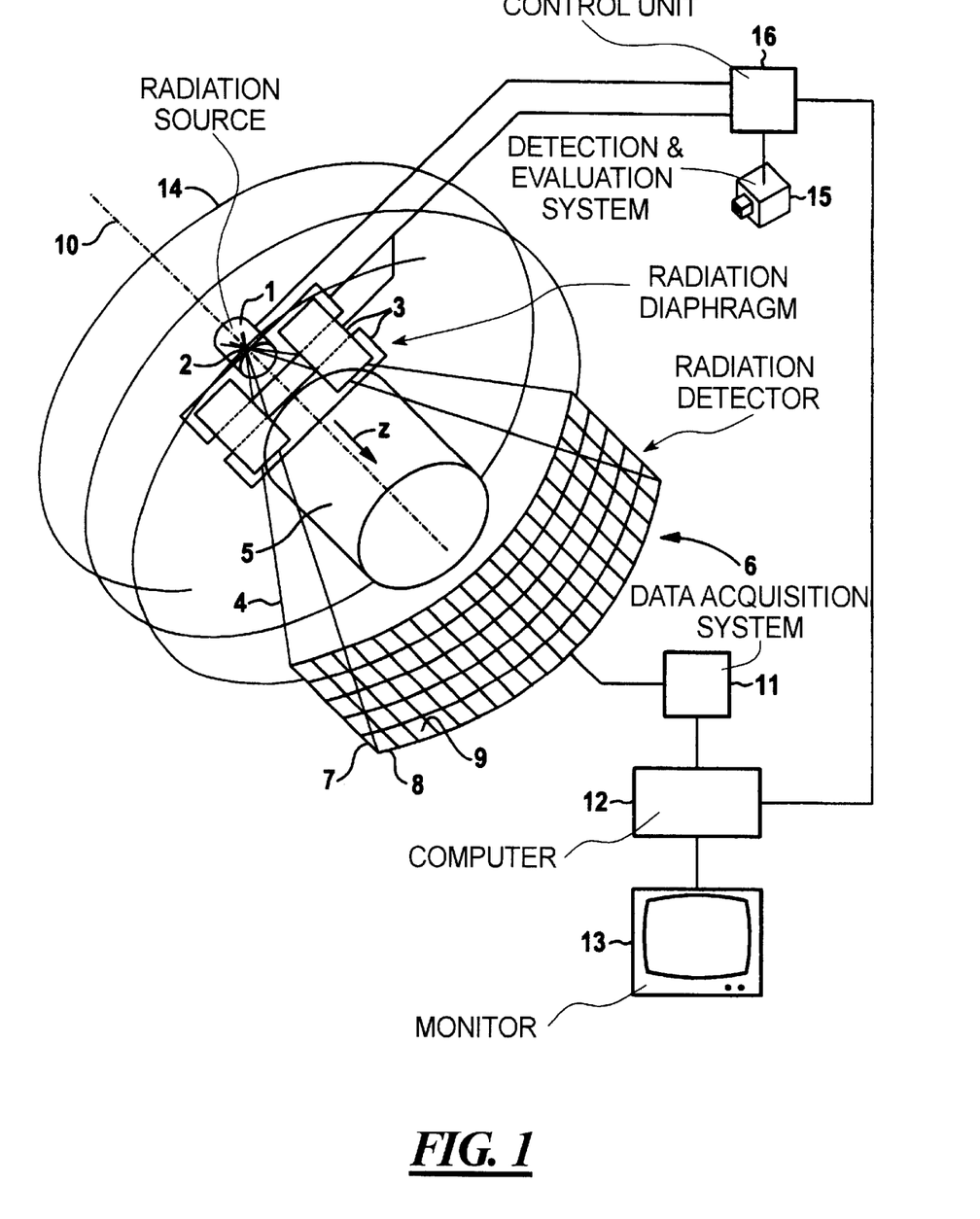
FIG. 1 shows a CT device according to the invention in an illustration which is partially a block diagram.

A CT device according to the invention is schematically shown in FIG. 1. The CT device has a radiation source 1, for example an X-ray tube, with a focus 2, from which a pyramidal radiation beam 4 emanates and which proceeds through a radiation diaphragm 3 at the tube. The beam 4 penetrates an object 5 under examination, for example a patient, and strikes a detector system 6. The detector system 6 is an array of parallel rows 7 and parallel columns 8, not necessarily of the same width, of detector elements 9. The radiation source 1 and the detector system 6 form a measuring system which can be displaced around a system axis 10. The measuring system 1, 6 and the object 5 under examination can be displaced relative to one another along the system axis 10 such that the object 5 under examination can be transirradiated along the system axis 10 at different projection angles and in different z-positions. A data acquisition system 11 uses the output signals of the detector elements 9 of the detector system 6 to form measured values, which are fed to a computer 12 which calculates an image of the object 5 under examination. This image is reproduced on a monitor 13.

The X-ray CT device according to FIG. 1 can be used both for sequential scanning and for spiral scanning. In the case of sequential scanning, the object 5 under examination is scanned in sections. In this process, the radiation source 1 is displaced with respect to the system axis 10 around the object 5 under examination, and the measuring system 1, 6 obtains a multiplicity of projections in order to be able to build up a two-dimensional tomographic image of a section of the object 5 under examination. The object 5 under examination is moved into a new z-position between the scanning of successive sections. This process is repeated until all sections which include the region to be reconstructed are covered.

During spiral scanning, the measuring system 1, 6 moves continuously on a spiral path 14 relative to the object 5 under examination until the region to be reconstructed is completely covered. A volumetric data record (dataset) is generated in the process. The computer 12 uses an interpolation method to calculate therefrom a planar data record from which it is then possible to reconstruct the desired images as in the case of sequential scanning.

A detection and evaluation system 15 detects the size, position and movement of objects which are located outside the object 5 under examination in the examination space penetrated by the X-ray radiation. This is an examiner's hand, for example. In accordance with the invention, the radiation is automatically reduced in the volumetric region of the examination space in which the hand is located. This is performed in the exemplary embodiment by a control unit 16, which both acts on the radiation source 1 and temporarily lowers the radiant power, and influences the position of the radiation diaphragm 3.

Figure 2:
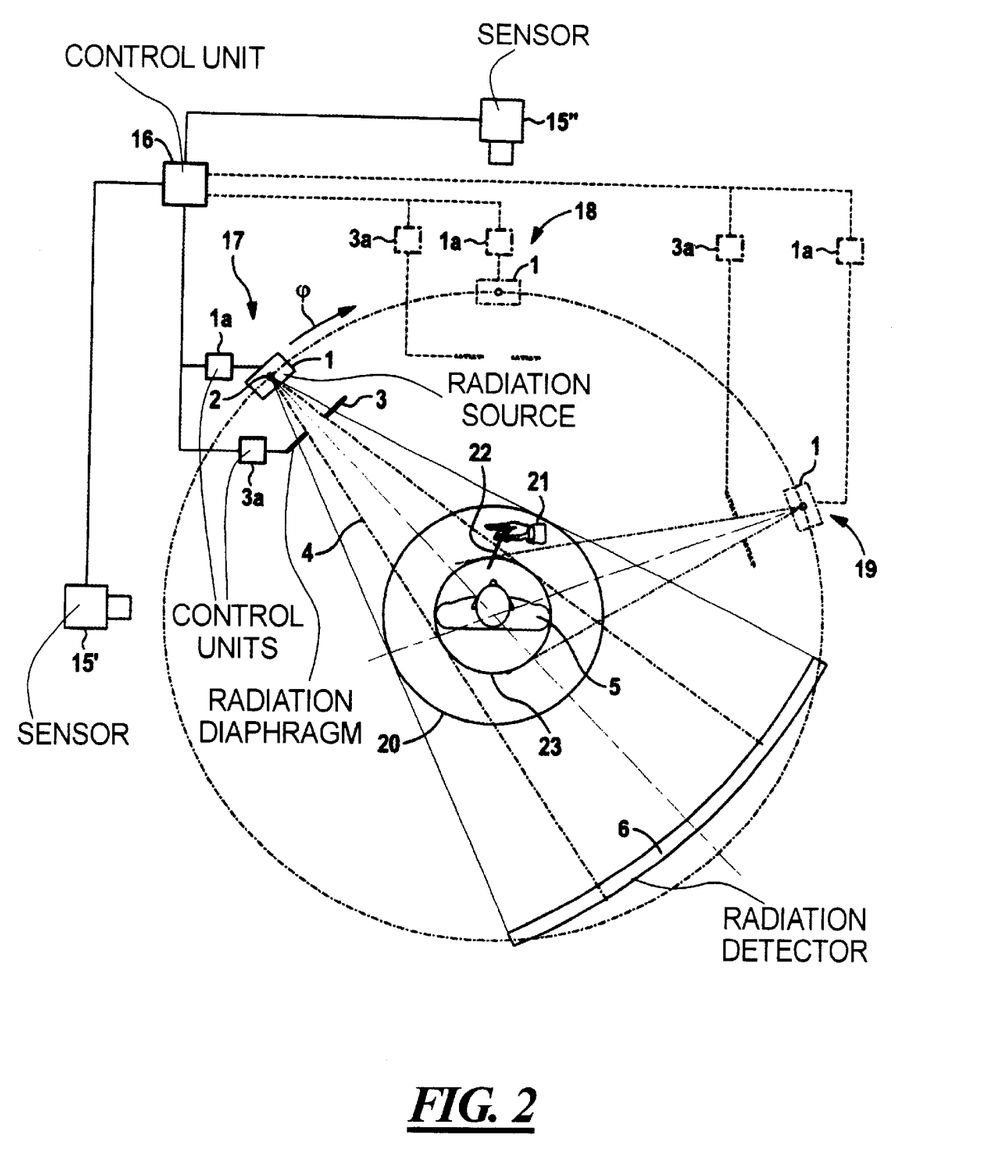
FIGS. 2, 5 and 6 show the measuring system of a CT device in accordance with FIG. 1, with an examiner's hand located in the examination space thereof.

FIG. 2 shows the measuring system 1, 6 of the CT device for different focal positions 17, 18 and 19, the detector system 6 being illustrated only for the focal position 17, for improved clarity. An examiner's hand 21 which holds a medical instrument 22, for example a needle, is located inside the examination space 20, and thus in the region covered by the radiation beam 4. The detection and evaluation system has two sensors 15' and 15", designed as cameras in the exemplary embodiment, for detecting the size and position of the hand 21 in the examination space 20. The data thereby obtained are transmitted to the control unit 16, which controls the radiant power of the radiation source 1 and the setting of the radiation diaphragm 3. For this purpose, the CT device has a control unit 1a for setting the tube current, for example a controlled current source, and control unit 3a for setting the radiation stop, for example electric drives. Without having to accept impairment of the quality of the images produced, the cross-section of the radiation beam 4 is already adapted to the object 5 under examination, such that during scanning the object 5 under examination is still precisely situated completely inside a measuring field 23 penetrated by the radiation beam 4. Focal positions for which the object 5 under examination is located between the hand 21 and the focus 2 are less dangerous for the examiner, since here a majority of the radiation already is absorbed by the object 5 under examination and therefore no longer constitutes a radiation stress for the hand 21. Moreover, for these focal positions, the spacing of the radiation source 1 from the hand 21 is relatively large, and this likewise diminishes the radiation dose, which is proportional to the square of the spacing. Consequently, the protective measures to be provided are concentrated, in particular, on the focal positions in which the hand 21 is located relatively close to the radiation source 1 and can be struck by the undiminished radiation. The focal position 17 is the focal position for which the hand 21 precisely enters the region covered by the radiation beam 4 in the case of rotation of the radiation source 1 in the φ-direction around the object 5 under examination. Because of the simple geometrical relationships (compare FIG. 3) in conjunction with the size and position of the hand 21 as determined by the sensors 15' and 15", this focal position 17 and the focal position 19 (in which the hand is situated once again precisely completely outside the radiation beam 4) can be calculated exactly. The control unit 16 then, for example, controls the tube current automatically so that no X-ray radiation emanates from the X-ray tube between the focal positions 17 and 19. This is indicated in the exemplary embodiment for the focal position 18.

In this case, controlling the tube current is only one possibility for automatically reducing the radiation dose fed to the hand 21. In another version of the invention the radiation diaphragm 3 is set (adjusted) dynamically during scanning by the control unit 16 and the control unit 3a, such that the hand 21 is not struck by the radiation.

Figure 3:
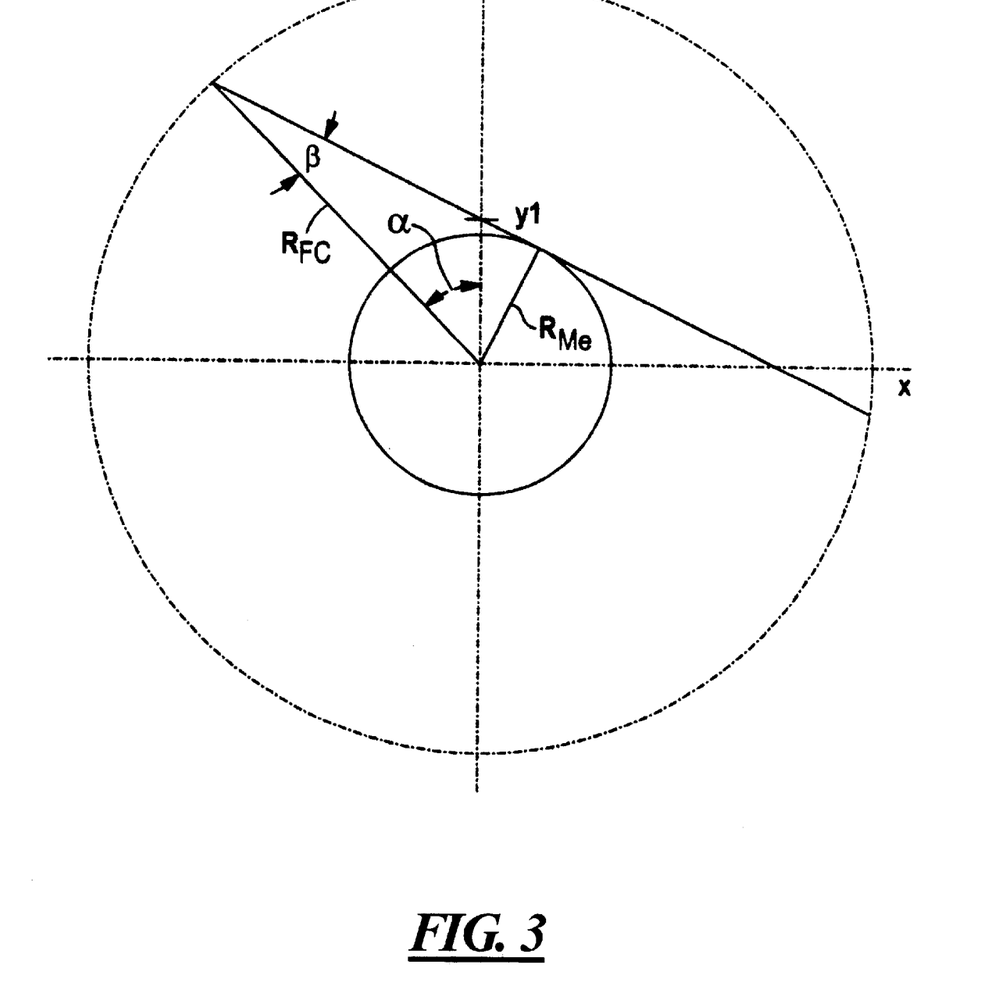
FIG. 3 shows geometrical relationships for explaining the invention.

FIG. 3 illustrates, as an example, geometrical quantities which can be used in an algorithm for controlling the radiation diaphragm 3 or the tube current. A Cartesian coordinate system with the origin of coordinates on the system axis 10 is oriented such that the part of the hand 21, for example a fingertip, which is first covered by the radiation beam 4 during scanning is situated on the y-axis. $R_{Fc}$ stands for the spacing of the focus 2 from the system axis 10 (compare FIG. 1), and $R_{Me}$ stands for the radius of the measuring field. The angular range which the focus 2 sweeps during rotation, starting from the position at which the radiation beam just touches the fingertip, to the position at which the focus is situated on the y-axis, is denoted as the switch-off angle α The spacing of the fingertip from the system axis 10 is determined by the detection and evaluation system 15 (compare FIG. 2) and is denoted by y1. For the half fan angle β in accordance with FIG. 3:

$$\frac{y1}{\sin\beta} = \frac{R_{Fc}}{\sin(\alpha + \beta)}$$

$$\beta = \arctan\frac{\sin\alpha}{\frac{R_{Fc}}{y1} - \cos\alpha}$$

This yields the following radius $R_{Me}$ of the measuring field:

$$R_{Me} = R_{Fc} \sin\beta$$

Figure 4:
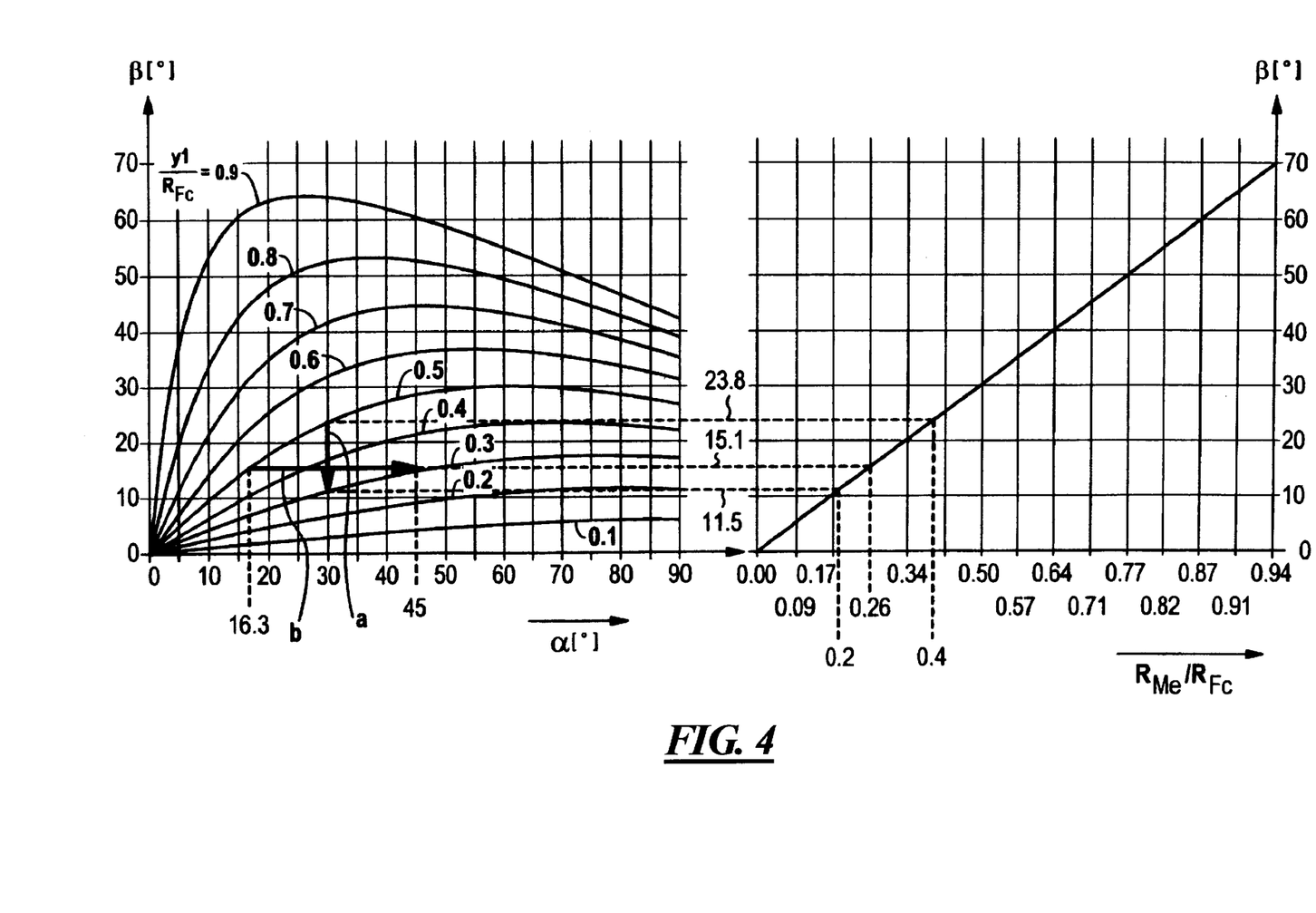
FIG. 4 shows two related diagrams for explaining the invention.

The angle β is plotted in the left diagram in FIG. 4 as a function of the switch-off angle α and of the normalized spacing of the fingertip from the system axis 10. If, for example, the normalized spacing of the fingertip from the system axis is $y1/R_{Fc}=0.5$, then a value for the angle β=23.8° results for a prescribed switch-off angle α=30°. The normalized radius of the measuring field is therefore calculated as $R_{Me}/R_{Fc}=0.4$. If the hand is guided from $y1/R_{Fc}=0.5$ to $y1/R_{Fc}=0.3$, and the switch-off angle is retained as α=30°, the angle β must be reduced from β=23.8° to β=15.1°. This relationship is illustrated graphically in the left diagram in FIG. 4 arrow a, in conjunction with the right diagram.

The switch-off angle α is only one possible parameter which can be preset for automatic control. In another version, for example, the maximum angular range for which the radiation is switched off is set. In FIG. 2, this corresponds to the angle enclosed by the straight lines respectively passing through the focal positions 17 and 19, and the system axis 10. It is also possible, for example, to set a minimum measure of the radius $R_{Me}$ of the measuring field, from which the CT device calculates the associated switch-off angle depending on the size and instantaneous position of the hand 21. This relationship is also illustrated graphically in FIG. 4. If, for example, $R_{Me}/R_{Fc}=0.26$ (right diagram), the movement of the hand from $y1/R_{Fc}=0.5$ to $y1/R_{Fc}=0.3$ leads, as follows from the left diagram, arrow b, to an enlargement of the switch-off angle α from α=16.3° to α=45°.

If a number of parameters are preset simultaneously, the CT device automatically controls the extent of the volumetric region in which the examiner's hand 21 is located and for which the radiation dose is reduced, taking all of the prescribed parameters into account. Such a setting is, for example:

$$\alpha < 30°$$

$$R_{Me}/R_{Fc} > 0.2.$$

Figure 5:
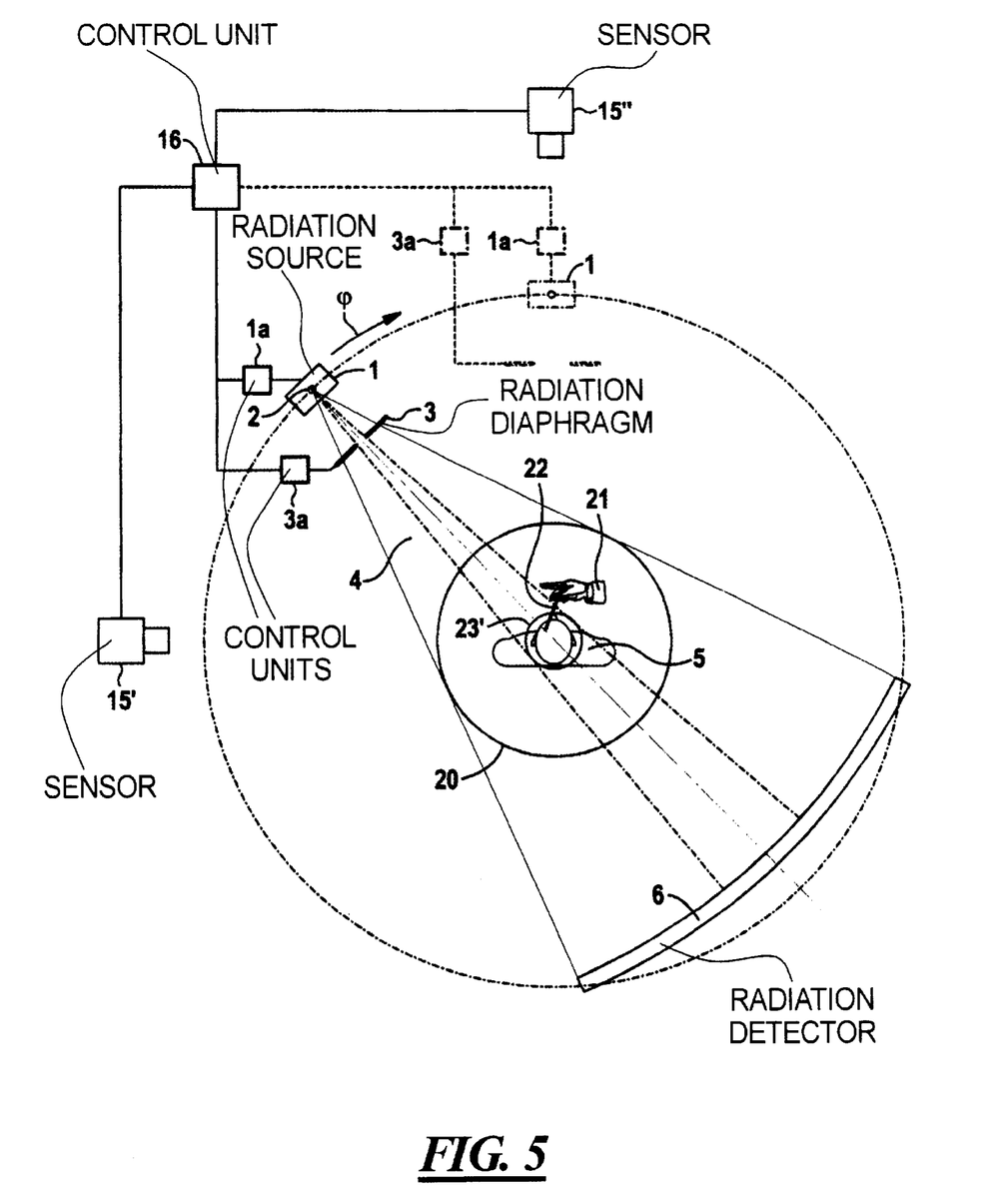

By comparison with FIG. 2, in the situation illustrated in FIG. 5 the examiner's hand 21 is brought closer to the object 5 under examination. This is detected by the two sensors 15' and 15", and the control unit 16 acts on the radiation diaphragm 3 to diminish the cross-section of the radiation beam 4. The setting of the radiation diaphragm 3 is then retained until the hand 21 essentially does not change position. The measuring field 23' is thereby reduced to the size illustrated in FIG. 5. The protection of the hand 21 against unattenuated radiation is achieved in the example, as described in the discussion of FIG. 2, by controlling the tube current. Because of the diminution of the measuring field 23', the detected segment of the object 5 under examination can be reproduced in a correspondingly enlarged fashion, and this improves the reproduction of detail and the possibility of navigating with the medical instrument.

Figure 6:
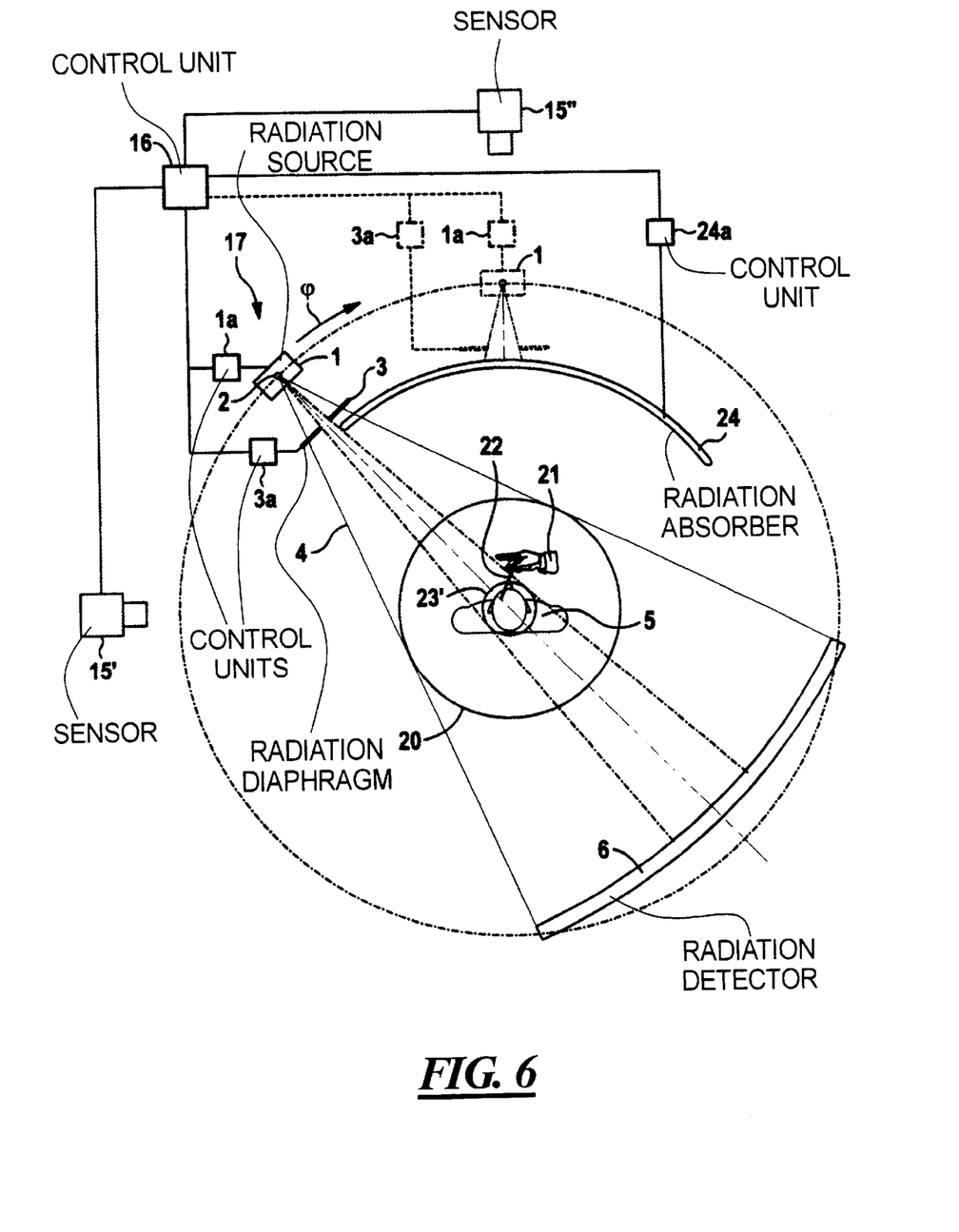

FIG. 6 illustrates an embodiment in which an absorber 24 is inserted into the beam path between the focus 2 and the hand 21 in order to protect the hand 21. In the illustrated embodiment, the absorber 24 does not rotate with the radiation source 1 around the object 5 under examination, and can be set by the control unit 16 and a control unit 24a.

It is, of course, also possible to use a combination of these techniques to limit the radiation dose to the hand 21. Thus, the measuring field can be diminished by setting the radiation diaphragm 3, the radiant power can be temporarily lowered by varying the tube current and, in addition, an absorber 24 can be active for a specific z-region and angular range.

The exemplary embodiments described above relate to CT devices of the third generation, wherein the X-ray source and the detector rotate jointly about the system axis during the production of images. However, the invention also can be used with CT devices of the fourth generation, in which only the X-ray source rotates and interacts with a fixed detector ring.

The exemplary embodiments described above relate to the medical application of CT devices according to the invention, however, the invention also can be applied outside medicine, for example in baggage inspection or in material testing.

Although modifications and changes may be suggested by those skilled in the art, it is the intention of the inventors to embody within the patent warranted hereon all changes and modifications as reasonably and properly come within the scope of their contribution to the art.

I claim as my invention:

1. A method for scanning an examination subject comprising the steps of:

disposing an examination subject in a computed tomography scanner having an x-ray radiator with a focus from which an x-ray beam emanates, and having a radiation detector;

scanning said examination subject in said scanner by rotating at least said focus around a system axis to irradiate said subject from a plurality of different directions, said detector system producing scanning data dependent on x-rays incident thereon respectively from said different directions;

during said scanning of said subject, automatically detecting entry of a body part of an examiner into a first volumetric region and, upon detection of entry of said body part into said region, automatically reducing an effective amount of said x-rays in said first volumetric region, compared to an effective amount of x-rays in a second volumetric region of a same size and at a same distance from said system axis in which no body part of the examiner is disposed; and detecting parameters associated with said body part of said examiner selected from the group consisting of size, position and movement direction, and automatically setting a size of said first volumetric region dependent on at least one of said parameters.

2. A method as claimed in claim 1 comprising detecting movement of said body along said system axis as one of said parameters, and setting said size of said first volumetric region dependent on said movement of said body part along said system axis.

3. A method as claimed in claim 1 wherein, at each of said different directions, said x-ray beam exhibits an angular range, and wherein said method comprises the step of detecting the angular range of a segment in which said body part of said examiner is located, as one of said parameters, and setting said size of said first volumetric region dependent on said angular range.

4. A method as claimed in claim 1 comprising detecting a spacing of said body part of said examiner from said system axis, as one of said parameters, and setting said size of said first volumetric region dependent on said spacing.

5. A method as claimed in claim 1 comprising continuously detecting movements of said body part during said scanning as successive parameters in said group of parameters, and periodically re-dimensioning said first volumetric region dependent on said movements.

6. A method as claimed in claim 1 comprising continuously detecting movements of said body part during said scanning as successive parameters in said group of parameters, and continuously re-dimensioning said first volumetric region dependent on said movements.

7. A method as claimed in claim 1 wherein the step of automatically reducing the effective amount of x-rays in said first volumetric region comprises reducing a cross-section of said x-ray beam.

8. A method as claimed in claim 1 wherein said x-ray radiator operates a radiant power, and wherein the step of reducing the effective amount of radiation in said first volumetric region comprises temporarily lowering said radiant power.

9. A method as claimed in claim 1 wherein the step of automatically reducing the effective amount of radiation in said first volumetric region comprises absorbing a portion of the x-rays emitted from said x-ray radiator.

10. A method as claimed in claim 1 wherein said scanning data comprise respective datasets from a plurarlity of projections, respectively for said different directions, and comprising the additional step of interpolating data from projections in which the effective amount of radiation in said first volumetric region was reduced using data from projections obtained without said effective amount of radiation in said first volumetric region being reduced.

11. A method as claimed in claim 1 wherein said scanning data comprise respective datasets from a plurarlity of projections, respectively for said different directions, and comprising the additional step of replacing data from projections in which the effective amount of radiation in said first volumetric region was reduced with data from projections obtained without said effective amount of radiation in said first volumetric region being reduced.

12. A method as claimed in claim 1 wherein said scanning data comprise a plurality of projection datasets respectively for said different directions, with pairs of said datasets for respective directions which are offset by 180 degrees from each other being complementary datasets, and wherein said method comprises the additional step of replacing the projection data in a projection dataset wherein the effective amount of radiation in said first volumetric region was reduced with the projection data from the projection dataset complementary thereto.

13. A computed tomography apparatus comprising:

a computed tomography scanner having an x-ray source with a focus from which an x-ray beam emanates, and a radiation detector, at least said focus of said x-ray source being rotatable around a system axis to irradiate an examination subject, disposed in said scanner, from a plurality of different directions, with said radiation detector producing scanning data dependent on x-rays incident thereon from the respective directions;

a detector arrangement for automatically detecting entry of a body part of an examiner into a first volumetric region covered by said x-ray beam;

a radiation control arrangement, connected to said detector arrangement, and interacting with at least one of said x-ray radiator and said x-ray beam for, upon detection of entry of a body part of said examiner into said first volumetric region, automatically reducing an effective amount of x-rays in said first volumetric region compared to an effective amount of x-rays in a second volumetric region of a same size and at a same distance from said system axis as said first volumetric region in which no body part of said examiner is disposed; and a dimensioning control arrangement, connected to said detector arrangement, for automatically setting a size of said first volumetric region dependent on at least one parameter associated with said body part selected from the group of parameters consisting of size, position and movement direction of said body part.

14. A computer tomography apparatus as claimed in 13 wherein said radiation control arrangement includes a radiation diaphragm disposed in a path of said x-ray beam, and wherein said radiation diaphragm is operated to reduce a cross-section of said x-ray beam to reduce the effective amount of radiation in said first volumetric region.

15. A computed tomography apparatus as claimed in claim 13 wherein said x-ray radiator operates at a radiant power, and wherein said radiation control arrangement temporarily lowers said radiant power to reduce the effective amount of radiation in said first volumetric region.

16. A computed tomography apparatus as claimed in claim 13 wherein said radiation control arrangement includes a radiation absorber insertable into a path of said x-ray beam to reduce said effective amount of radiation in said first volumetric region.

* * * * *